(12) United States Patent
Neumann

(10) Patent No.: US 12,704,938 B2
(45) Date of Patent: Aug. 11, 2026

(54) METHODS AND SYSTEMS FOR PROVIDING ALIMENTARY ELEMENTS

(71) Applicant: KPN INNOVATIONS, LLC., Lakewood, CO (US)

(72) Inventor: Kenneth Neumann, Lakewood, CO (US)

(73) Assignee: KPN Innovations LLC, Lakewood, CO (US)

( * ) Notice: Subject to any disclaimer, the term of this patent is extended or adjusted under 35 U.S.C. 154(b) by 281 days.

(21) Appl. No.: 18/225,503

(22) Filed: Jul. 24, 2023

(65) Prior Publication Data

US 2023/0400962 A1 Dec. 14, 2023

Related U.S. Application Data

(63) Continuation-in-part of application No. 17/892,915, filed on Aug. 22, 2022, now Pat. No. 11,740,768, which is a continuation of application No. 17/387,245, filed on Jul. 28, 2021, now Pat. No. 11,429,254, which is a continuation of application No. 17/106,487, filed on Nov. 30, 2020, now Pat. No. 11,106,335.

(51) Int. Cl.

| | |
|---|---|
| ***G06F 3/0482*** | (2013.01) |
| ***G06F 9/54*** | (2006.01) |
| ***G06N 20/00*** | (2019.01) |
| ***G16B 10/00*** | (2019.01) |
| ***G16H 20/60*** | (2018.01) |

(52) U.S. Cl.
CPC ........... *G06F 3/0482* (2013.01); *G06F 9/542* (2013.01); *G06N 20/00* (2019.01); *G16B 10/00* (2019.02); *G16H 20/60* (2018.01)

(58) Field of Classification Search
CPC ......... G06F 3/048; G06F 9/452; G16H 20/60; G06N 20/00
USPC .......................................................... 715/764
See application file for complete search history.

(56) References Cited

U.S. PATENT DOCUMENTS

| | | | | |
|---|---|---|---|---|
| 10,553,316 | B1 | 2/2020 | Neumann | |
| 10,580,533 | B2 * | 3/2020 | Sati | G16H 20/60 |
| 10,825,567 | B1 * | 11/2020 | Wala | G16H 10/60 |
| 11,501,867 | B2 * | 11/2022 | Mairs | G16H 20/17 |

(Continued)

*Primary Examiner* — William D Titcomb
(74) *Attorney, Agent, or Firm* — Caldwell LLC

(57) ABSTRACT

A system for providing alimentary elements includes a computing device configured to receive a primary input relating to a first user for a compatible alimentary element based on biological extraction, receive secondary input from the second user for an alimentary element not associated with biological extraction, generate an extensible alimentary element display for the second user, wherein generating the extensible alimentary element display includes locating at least an alimentary element originator as a function of the secondary input and the compatible alimentary elements, generating a queue of alimentary elements from the located alimentary element originator, wherein the queue includes alimentary elements for the second user as a function of the secondary input and compatible alimentary elements for the first user, and provide a representation, via a graphical user interface, of a compatible alimentary element for the first user and an alimentary element for the second user.

20 Claims, 8 Drawing Sheets

(56) References Cited

U.S. PATENT DOCUMENTS

| | | | | |
|---|---|---|---|---|
| 11,568,351 | B2* | 1/2023 | Neumann | G16H 50/20 |
| 2002/0128992 | A1* | 9/2002 | Alabaster | G16H 15/00 |
| 2012/0136731 | A1* | 5/2012 | Kidron | G16H 10/60 705/15 |
| 2014/0033050 | A1* | 1/2014 | Shin | H04N 21/4788 715/733 |
| 2014/0287384 | A1* | 9/2014 | Boyes | G09B 5/02 434/127 |
| 2016/0166195 | A1* | 6/2016 | Radecka | A61B 5/112 600/595 |
| 2020/0043595 | A1* | 2/2020 | Ohyama | G06V 20/20 |
| 2020/0082169 | A1* | 3/2020 | Lu | G08B 21/0476 |
| 2020/0321111 | A1* | 10/2020 | Neumann | G06N 5/02 |
| 2020/0342353 | A1* | 10/2020 | Neumann | G06N 20/00 |
| 2020/0356864 | A1* | 11/2020 | Neumann | G06N 3/0464 |
| 2020/0380458 | A1* | 12/2020 | Neumann | G06Q 10/0832 |
| 2020/0380459 | A1* | 12/2020 | Neumann | H04L 67/306 |
| 2021/0074403 | A1* | 3/2021 | Neumann | G16H 50/20 |
| 2021/0141620 | A1* | 5/2021 | Magureanu | G06F 8/38 |
| 2022/0036215 | A1* | 2/2022 | Neumann | G06N 20/00 |

* cited by examiner

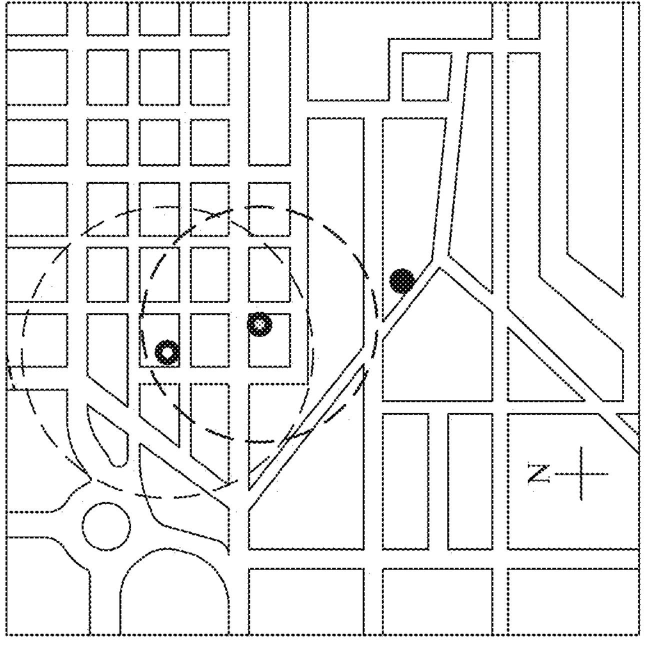
FIG. 5B
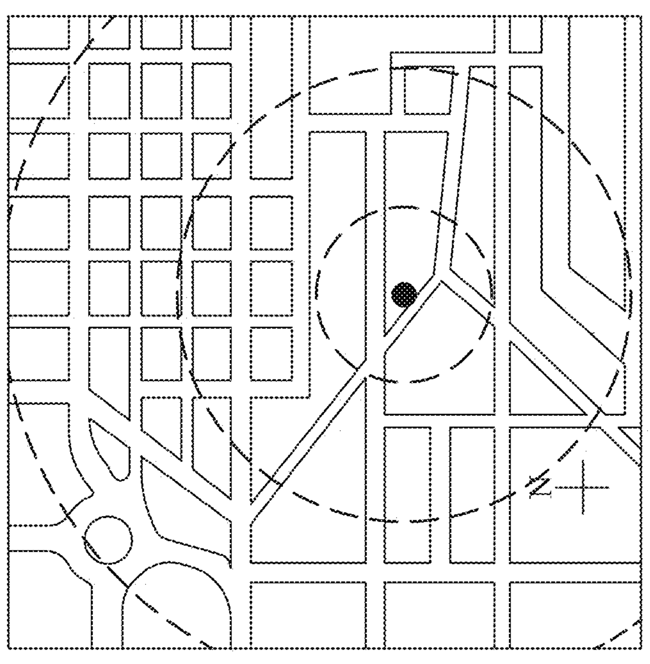
FIG. 5A

METHODS AND SYSTEMS FOR PROVIDING ALIMENTARY ELEMENTS

CROSS-REFERENCE TO RELATED APPLICATIONS

This application is a continuation-in-part of Non-provisional application Ser. No. 17/892,915, filed on Aug. 22, 2022, and entitled "METHODS AND SYSTEMS FOR PROVIDING ALIMENTARY ELEMENTS," which claims the benefit of priority to Non-provisional application Ser. No. 17/387,245, filed on Jul. 28, 2021, and entitled "METHODS AND SYSTEMS FOR PROVIDING ALIMENTARY ELEMENTS," which claims the benefit of priority to Non-provisional application Ser. No. 17/106,487 filed on Nov. 30, 2020, and entitled "METHODS AND SYSTEMS FOR PROVIDING ALIMENTARY ELEMENTS," the entirety of each of these applications are incorporated herein by reference.

FIELD OF THE INVENTION

The present invention generally relates to the field of graphical user interface and document processing. In particular, the present invention is directed to methods and systems for providing alimentary elements.

BACKGROUND

Updating graphical user interface presentation of elements aimed at improving physiology is typically based on returning solutions determined through computer software. Generating newer options as a function of the multiplicity of feedback, such as taste, preference, and nutrition are difficult to achieve while being mindful of individual physiology without designated inputs.

SUMMARY OF THE DISCLOSURE

In an aspect, a system for providing alimentary elements is disclosed. The system includes a computing device. The computing device is configured to receive a secondary input from a second user, wherein the secondary input includes at least a request for a compatible alimentary element of a first user. The computing device is configured to generate an alimentary element program as a function of the compatible alimentary element and a biological extraction associated with the first user. The computing device is configured to locate at least an alimentary element originator as a function of a first position associated with the first user and the compatible alimentary element. The computing device is configured to generate a queue of a plurality of alimentary elements from the at least an alimentary element originator, wherein the queue of alimentary elements comprises a plurality of alimentary element. The computing device is configured to display the queue of a plurality of alimentary elements using a graphical user interface.

In another aspect, a method for providing alimentary elements is disclosed. The method includes receiving, using a computing device, a secondary input from a second user, wherein the secondary input includes at least a request for a compatible alimentary element of a first user. The method includes generating, using the computing device, an alimentary element program as a function of the compatible alimentary element and a biological extraction associated with the first user. The method includes locating, using the computing device, at least an alimentary element originator as a function of the compatible alimentary element. The method includes generating, using the computing device, a queue of a plurality of alimentary elements from the at least an alimentary element originator, wherein the queue of alimentary elements comprises a plurality of alimentary element. The method includes displaying the queue of a plurality of alimentary elements using a graphical user interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 5A and 5B are a diagrammatic representation of an exemplary embodiment of a locating an alimentary element originator using radial search;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for providing alimentary elements. In an embodiment, the system includes a computing device configured to receive input from a first user corresponding to an alimentary element that is generated as a function of the first user's biological extraction data. Computing device is further configured to receive input from a second user for an alimentary element that does not contain the same corresponding data. The computing device is configured to generate an extensible alimentary element display that may generate alimentary elements for the second user as a function of the alimentary element originators in proximity to the location of the two users. In an embodiment, system may generate metrics so that second user may make an alimentary element selection based on nutrition, like how the first user is provided alimentary elements.

Figure 1:
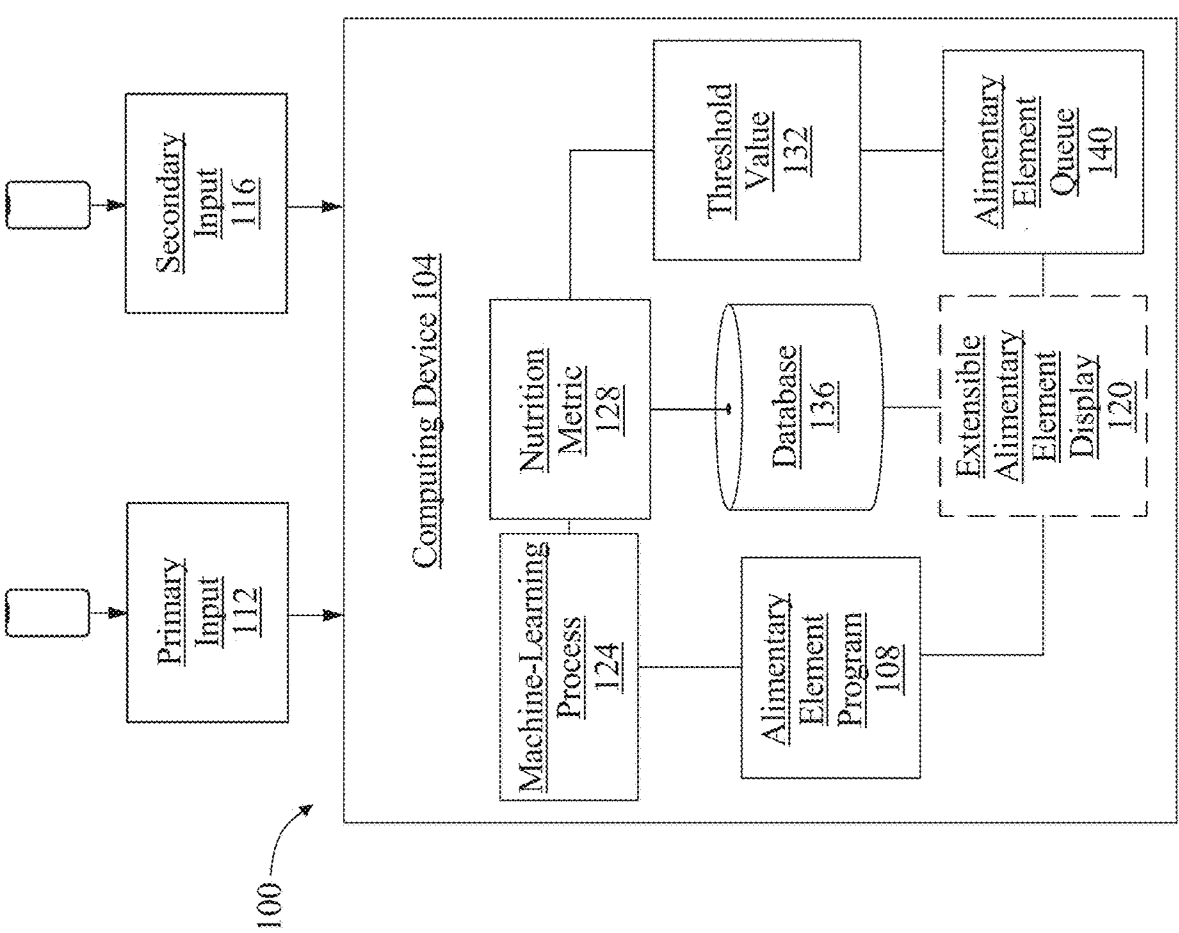
FIG. 1 is a block diagram illustrating an exemplary embodiment of a system for providing alimentary elements.

Referring now to FIG. 1, an exemplary embodiment of a system 100 for providing alimentary elements is illustrated.

System includes a computing device 104. Computing device 104 may include any computing device as described in this disclosure, including without limitation a microcontroller, microprocessor, digital signal processor and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 receive primary input relating to a first user for a compatible alimentary element, wherein compatible alimentary elements are based on biological extraction received from the first user. As used in this disclosure, an "alimentary element," is a meal, grocery item, food element, beverage, nutrition supplement, edible arrangement, or the like, that may be generated by a restaurant, cafeteria, fast food chain, grocery store, food truck, farmer's market, proprietor, convenience store, deli, or any place that provides the above to an individual. A "compatible alimentary element," as used in this disclosure, is an alimentary element provided to an individual according to the individual's biological extraction data, wherein alimentary elements are "compatible" based on a determination regarding the compatibility of the alimentary elements according to the biological extraction data. "Biological extraction" data, as used in this disclosure, is chemical data, physiological data, medical data, and the like. A compatible alimentary element may include alimentary elements intended to address a nutrition deficiency, reduce inflammation, improve recovery from exercise, improve overall health, among other targeted effects. A compatible alimentary element may include alimentary elements provided as a function of an individual's allergies, food intolerances, philosophical, religious, and lifestyle considerations, among other factors involved in selecting alimentary elements, for instance plant-based, vegan, Kosher, and the like. A compatible alimentary element may be generated and provided to a user as a function of a user's biological data, such as blood chemistry, for instance blood protein and enzyme concentrations and specific activities for instance of fibrinogen, ferritin, serum amyloid A, α-l-acid glycoprotein, ceruloplasmin, hepcidin, haptoglobin, tumor necrosis factor-α (TNF-α), among other acute phase proteins; for instance cytokine identities and concentrations for instance interleukin-6 (IL-6); metabolites identities and concentrations such as blood sugar, LDL and HDL cholesterol content; hormone identities and concentrations such as insulin, androgens, cortisol, thyroid hormones, and the like; erythrocyte sedimentation rate, blood cell counts, plasma viscosity, and other biochemical, biophysical, and physiological properties regarding blood panels, blood tests, and the like, for instance and without limitation as it relates to biomarkers of inflammation. Alimentary elements may be recommended to a user as a function of these biological extraction data with the intention of modifying the biological extraction data, for instance by lowering blood sugar, decreasing LDL cholesterol levels, reducing pro-inflammatory biomarkers, reducing free radicals and oxidative damage, among other targeted effects of alimentary elements on user biological extraction.

Continuing in reference to FIG. 1, in non-limiting illustrative examples, biomarkers of inflammation may include biochemical properties specific to a user such as the level of inflammation as evidence by the presence and concentration of inflammatory biomarkers, post-translational modification of proteins, epigenetic markers, etc., and alimentary elements may be identified and provided to a user to focus on reducing inflammation for instance and without limitation, as described in U.S. Nonprovisional application Ser. No. 17/007,251 filed Aug. 31, 2020 titled "METHOD OF SYSTEM FOR REVERSING INFLAMMATION IN A USER," the entirety of which is incorporated herein by reference. The level of inflammation, or any biochemical ailment and/or property of a user may be enumerated, and based on the numerical value, an alimentary element may be recommended to the user. Alternatively or additionally, user biological extraction may be used as an input for determining alimentary element recommendations that improve the user's health state based on the user's biological extraction, for instance and without limitation, as described in U.S. Nonprovisional application Ser. No. 16/375,303 filed Apr. 4, 2020 titled "SYSTEMS AND METHODS FOR GENERATING ALIMENTARY INSTRUCTION SETS BASED ON VIBRANT CONSTITUTION GUIDANCE," the entirety of which is incorporated herein by reference.

Continuing in reference to FIG. 1, computing device 104 is configured to receive primary input relating to a first user for a compatible alimentary element. As described above, compatible alimentary elements may be provided to a user as a function of a user's individual alimentary element program, which may be informed by a user's biological extraction data. An "alimentary element program," as used in this disclosure, is a plurality of compatible alimentary elements as defined above, which a user may be informed to select based on a user's biological extraction, including medical data, physiology, demographics, lifestyle, and the like. An alimentary element program 108 may include, for instance and without limitation, an instruction set that a computing device 104 may provide to a user concerning alimentary elements that may improve the user's health state, including meal-types, macronutrient amounts, nutrient quantities, appropriate times to eat, among other data. An alimentary element program 108 may include alimentary elements a user is expected to substitute to avoid ailments such as allergies, food intolerances, inflammation, and the like. An alimentary element program 108 may include alimentary elements a user is expected to include in their diet to address nutrition deficiencies, symptoms, diseases, and the like. In non-limiting illustrative examples, an alimentary element program 108 may be associated with an audiovisual notification, wherein the notification is used by computing device 104 to provide a compatible alimentary element obtained from the alimentary element program 108 directed to be displayed to the user via a user device, such as a "smartphone", laptop, tablet computer, internet-of-things (IOT) device, and the like.

Continuing in reference to FIG. 1, a "primary input," as used in this disclosure, is an input for receiving an alimentary element, for instance from an alimentary element program 108, by a user that has compatible alimentary elements. Primary input 112 may include user input from a graphical user interface. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the user and accept input from the user. Graphical user interface may accept user input, wherein user input may include an interaction with a user device. A user device may include computing device 104, a "smartphone," cellular mobile phone, desktop computer, laptop, tablet computer, internet-of-things (IOT) device, wearable device, among other devices. User device may include any device that is capable for locating and/or ordering alimentary elements via a data network technology such as 3G, 4G/LTE, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, etc.), and the like.

Continuing in reference to FIG. 1, computing device 104 is configured to receive secondary input relating to a second user for an alimentary element, wherein the second user is not associated with an alimentary element program 108. As used in this disclosure, "secondary input," is input for an alimentary element by a user that has not provided biological extraction data for the purpose of determining compatible alimentary elements. Secondary input 116 may include input, as described above for primary input, which is received by computing device 104 via a graphical user interface. Secondary input 116 may include input from a user via an interaction with a user device, as described above. In some embodiments, secondary input 116 may include primary input 112. As a non-limiting example, secondary input 116 may include a request for alimentary element for a first user. As a non-limiting example, secondary input 116 may include an alimentary order for a first user.

With continued reference to FIG. 1, second user may include a person who knows first user. As non-limiting examples, second user may include a friend, family member, neighbor or the like. In some embodiments, second user may include a healthcare provider of first user. In some embodiments, second user may include an organization or group of individuals. As a non-limiting example, second user may include a place of work of first user. As a non-limiting example, second user may include a club to which first user is a member.

With continued reference to FIG. 1, secondary input 116 may include payment information. "Payment information," for the purposes of this disclosure, is information that enables alimentary elements to be purchased. As non-limiting examples, payment information may include credit card information, a bank account number, authentication for an online payment provider (such as PAYPAL), and the like. In some embodiments, computing device 104 may use payment information to purchase one or more alimentary elements. In some embodiments, payment information from secondary input 116 may be used to purchase alimentary elements for a first user.

With continued reference to FIG. 1, secondary input 116 may be received by computing device 104 through an application program interface (API). An "API," for the purposes of this disclosure, is a software interface that allows two or more computer programs to communicate with each other.

Continuing in reference to FIG. 1, computing device 104 is configured to generate an extensible alimentary element display for the second user, wherein generating the extensible alimentary element display includes locating alimentary element originators as a function of the secondary input and the compatible alimentary elements for the first user as a function of a first position associated with the first user. An "extensible alimentary element display," as used in this disclosure, is a display using an interaction technique, user interface technique, and/or input technique functioning as a combination of hardware and software elements that provides a way for at least a second user that has not provided biological extraction data, to locate, select, and/or order alimentary elements alongside a first user which has compatible alimentary elements provided. An extensible alimentary element display 120 is "extensible" in that the first user may not need to use such a display feature when inputting a request for a compatible alimentary element, but may require such a display feature when inputting multiple requests, for instance for multiple users, at least one of which is not associated with the alimentary element program 108 of the first user. An "interaction technique" starts when a user interacts with an application, causing an electronic device to respond, and includes direct feedback from the device to the user.

Continuing in reference to FIG. 1, an "alimentary element originator," as used in this disclosure, is any establishment and/or entity that may provide an alimentary element. An alimentary element originator may include a grocer, convenience store, fast-food chain, restaurant, health food store, nutrition supplement store, juice bar, or the like. An alimentary element originator may be simply referred to herein as an "originator."

Continuing in reference to FIG. 1, extensible alimentary element display 120 may include interaction platforms of differing levels of granularity, wherein interactions may take the form of alimentary element requests by a plurality of users. Interaction techniques are usually characterized at various levels of granularity, or the level of detail, or summarization, of the units of data in the database, computing network, server, and the like. For instance, the level of technology, platform, and/or implementation-dependent software and hardware for implementing the interaction platform. In non-limiting illustrative examples, extensible alimentary element display 120 may display to users the number and status of alimentary element originators according to their location for a single alimentary element request, representing a case of low-level granularity; however, the "hidden layers" of the extensible alimentary element display 120 operating on the computing device 104 may include data corresponding to the nutrition labels of the alimentary elements, such as caloric content, water soluble vitamins, fat soluble vitamins, macronutrient content, micronutrient content, the identity and number of compatible alimentary elements at each originator, among other data. In such an example, the granularity of the "hidden layers" of the extensible alimentary element display 120—not shown to the users—may carry data that is useful to computing device 104 for determining which alimentary elements to display, which originators to locate, etc. Interaction techniques exist that are specific to various devices, such as mobile devices, touch-based displays, traditional mouse/keyboard inputs, and other paradigms, in other words, they are dependent on a specific technology or platform. In contrast, viewed at higher levels of granularity, the interaction is not tied to any specific technology or platform. The interaction of 'filtering' alimentary elements, for example, can be characterized in a way that is technology-independent, for instance, performing an action where some information is hidden and only a subset of the original information remains or is displayed. Persons skilled in the art, upon review of the disclosure in its entirety, will be aware of such an interaction that may be implemented using any number of techniques, and on any number of platforms and technologies.

Continuing in reference to FIG. 1, extensible alimentary element display 120 may receive an interaction task, or "the unit of an entry of information by the users", such as entering a datum of text, issuing a command, or specifying a 2D position, for instance on a map. For instance, and without limitation, a first user's current location, as an address, GPS coordinates, or the like, that may specify a position on a 2D map, an indication that a specific type of meal (breakfast, lunch, dinner, etc.) is wanted, a specific price range for an alimentary element, or the like. A similar concept is that of domain object, which is a datum of application data that may be manipulated by the user, or even by the display application, such as scrolling through a queue, selecting a graphical icon, etc. Interaction techniques are the "glue" between physical I/O devices and interaction tasks, or domain objects. Different types of interaction techniques may be used to map a specific device to a specific domain object, for instance, in identifying a user's first position and identifying which establishments within a first radius of that location are alimentary element originators.

Continuing in reference to FIG. 1, extensible alimentary element display 120 may include any user interface (UI), graphical user interface (GUI), or interaction technique and/or method suitable for allowing user to submit primary input, secondary input, provide originators, alimentary elements, and the like. Extensible alimentary element display 120 may include 3D interaction techniques, different types of user interfaces, input devices, interaction designs, interactivity, information visualization, visual analytics, and graphical widgets (graphical control elements/controls). Persons skilled in the art, upon review of this disclosure in its entirety, will be aware the various methods, techniques, and technology suitable for implementing the extensible alimentary element display 120 for receiving primary input and second input data and providing alimentary elements.

With continued reference to FIG. 1, extensible alimentary element display 120 may be presented to second user. In some embodiments, extensible alimentary element display 120 may comprise an interactive graphical user interface that is configured to display alimentary elements on a second device associated with the second user. In some embodiments, interactive graphical user interface may be configured to display an onboarding element. An "onboarding element," for the purposes of this disclosure, is an element of a graphical user interface that is configured to introduce user to system 100. Onboarding element may include information regarding the operation of system 100. Onboarding element may include information regarding the benefits of system 100. In some embodiments, onboarding element may include a sign-up button. The sign-up button may allow a user, such as secondary user, to interact with it to create an account and/or create alimentary element program 108.

With continued reference to FIG. 1, primary input 112 and/or secondary input 116 may include a desired order time. A "desired order time," is a time at which an alimentary element or plurality of alimentary inputs are desired to be ready for consumption. In some embodiments, desired order time may include a time at which first or second user desires one or more alimentary elements to be delivered. In some embodiments, desired order time may include a time at which first or second user desires one or more alimentary elements to be ready for pickup and/or consumption from an alimentary provider.

Continuing in reference to FIG. 1, locating alimentary element originators as a function of the secondary input and the compatible alimentary elements for the first user as a function of a first position associated with the first user may include using a radial search algorithm. A "first position," as used in this disclosure, is a current location of a user. A first position may be the location of the first user, which may be the same location as a second user. Alternatively or additionally, the first user and second user may not be in the same location, in which case multiple locations may be used, wherein a first user wishes to place input for multiple alimentary elements destined for distinct locations and to be generated by distinct originators. Computing device 104 may determine a current location of a user (first position) by using a mapping algorithm, application, web-based mapping tool, or the like, for instance and without limitation GOOGLE MAPS and the Internet communicating with the GPS on a user device.

Continuing in reference to FIG. 1, computing device 104 may identify originators as a function of a hierarchy of instruction, for instance by first identifying an originator that can provide a compatible alimentary element for a first user, and that has at least a second option for the second user. Computing device 104 may locate at least an originator that provides a first compatible alimentary element for the first user, and a second, distinct compatible alimentary element that is compatible for the first user but is intended for the second user, etc.

Continuing in reference to FIG. 1, locating alimentary element originators may include using a radial search algorithm and/or any searching algorithm for instance radial or quadrant search, "nearest neighbors" machine-learning algorithms (nearest neighbor search), among other machine-learning algorithms, processes, methods, and non-machine-learning algorithms. For instance, computing device 104 may receive a first position datum from a user, for instance using GPS capability on a user device, and a mapping application such as GOOGLE MAPS, to identify the user first position on a 2D map. Computing device 104 may then search within a predefined distance, such as "walking distance", an arbitrary distance value (such as 1 mile), among other distance parameters, and retrieve signifiers associated with originators, such as restaurant names, menu items, and the like. Computing device 104 may then search menus, items lists, online data repositories, such as restaurant websites, and the like, for instance using a word-based query, to search for compatible terms to identify if an originator represents a solution.

Continuing in reference to FIG. 1, computing device 104 may locate alimentary element originators using a radial search machine-learning process to determine a first position and search a first distance relative to the first position for an originator. Locating an originator may include using a radial search machine-learning process, wherein the radial search machine-learning process determines a first search radius and searches the first radius for an alternative alimentary element originator, wherein the user can order at least a compatible alimentary element from the originator. A radial search machine-learning process may include machine-learning algorithms, processes, and/or models, performed by a machine-learning module, as described in further detail below. Radial search machine-learning process may execute a radial search, wherein the radial search may find approximate solutions to combinatorial problems. Combinatorial problems involve finding a grouping, ordering, clustering, or assignment of a discrete, finite set of objects (originators) that satisfies given conditions (compatible alimentary elements, cuisine-type, meal-type, price, etc.).

Continuing in reference to FIG. 1, a radial search machine-learning process may accept an input of a user geophysical location and a primary input and/or secondary input, and search within a first radius for an originator. Computing device 104 may then search the originator for an alimentary element that satisfies a criterion (compatible, meal-type, cuisine type, nutrient content, etc.), generating an output that describes the alimentary element, geophysical location, originator identity, among other data. Alternatively or additionally, a radial search machine-learning process may begin with a first originator geophysical location and menu, ingredient list, etc. as a "local solution" and select the first originator geophysical location as the center for a subsequent radial search. Radial search machine-learning process may place the primary input and/or secondary input data on a 2-Dimensional grid, for instance and without limitation, using a mapping application or algorithm such as a web-based navigation application such, a mobile navigation application, or the like, that may relate geophysical location in a predetermined area based on a first position using a computing device 104 and/or user device.

Continuing in reference to FIG. 1, radial search approach may include using the concept of distance rings, wherein each ring is a particular distance about a central location, which defines the location and size of search areas, perhaps about a current 'good' solution. For instance, a first originator that provides 'breakfast' and at least one compatible alimentary element may be a current 'good' solution, but a radial search may indicate a larger ring about the originator, searching further from that location for a second originator that provides 'lunch,' 'Chinese Food,' and at least a second compatible alimentary element. Radial search iteratively modifies the radii of these rings, and generates new centers, to cover the search space. A concentration step corresponds to choosing a solution (originator) as the center of a new ring. An expansion step corresponds to the exploration around a given center by increasing and reducing the radius of the ring until a better solution other than the current center is found. A "better solution" may include an originator that is nearer to a user, contains a compatible alimentary element, contains a specific modifier such as cuisine type, nutrient level, price, among other criteria. This dynamic process of centration and expansion of the search is repeated until a stopping condition is met. A stopping condition, for instance and without limitation, may be an originator that supplies an alimentary element a user has indicated is suitable, or otherwise a match to a compatible alimentary element in the alimentary element program 108 queue, and/or an alimentary element that is a minimal distance from user current first position.

Continuing in reference to FIG. 1, radial search may use any form of proximity search, or any algorithm used for solving an optimization problem of locating a point (originator) in a given set that is closest to a given point (user), provided a searching criterion (primary input/secondary input). Radial search algorithms, methods, and computational processes that radial search machine-learning process, as described herein, may include exact methods of proximity search including linear search and space partitioning; approximation methods such as Greedy search in proximity neighborhood graphs, locality sensing hashing, nearest neighbors search in spaces with small intrinsic dimension, projected radial search, vector approximation filing, and compression/clustering based search. Alternatively or additionally, radial search machine-learning processes may include variants of radial search methods and algorithms such as k-nearest neighbors, approximate nearest neighbors, fixed-radius near neighbors, and all nearest neighbors.

Continuing in reference to FIG. 1, locating alimentary element originators may include identifying alimentary element originators as a function of proximity to first position, and sorting the alimentary element originators based on the ability to provide compatible alimentary elements. A search criterion for locating originators may include the propensity to provide compatible alimentary elements based on a first user's biological extraction. Once an originator is located in this manner, computing device 104 may identify a menu, item list, or the like, and search for alimentary elements a second user may want. Second user may submit secondary input that indicates a variety of data such as desired price range, cuisine type, meal type, nutrition level, allergies, food intolerances, and the like, to refine the originator search. Computing device 104 may sort originators located relative to the first position by data elements identified in the primary input, such as the presence of a particular compatible alimentary element. Once a first solution (originator) is located, all other originators may be sorted, filtered, omitted, and returned as solutions based on the ability to provide at least a compatible alimentary element. Originators which cannot provide a compatible alimentary element, may be queued specifically in response to secondary input, wherein the user has no alimentary element program 108.

Continuing in reference to FIG. 1, the extensible alimentary element display 120 for the second user may include an interactive graphical user interface that is configured to display alimentary elements on a second device associated with the second user as a function of what is displayed on a first device associated with the first user. Extensible alimentary element display 120 may be shown to the first user on a first user device. Extensible alimentary element display 120 may be initiated on a first user device by the first user and shared with a second user so that the first user may select compatible alimentary elements from an alimentary element program 108, whereas the second user may find alimentary elements either at the same originator and/or different originator. Extensible alimentary element display 120 may display compatible alimentary elements to the first user but display different alimentary elements to a second user, whereas the display is informed based on location, nutrition, of submission by the first and/or second user, etc.

Continuing in reference to FIG. 1, computing device 104 is configured to generate a queue of alimentary elements retrieved from the located alimentary element originators, wherein the queue includes alimentary elements for the second user as a function of compatible alimentary elements provided to the first user. A "queue of alimentary elements," as used in this disclosure, is a collection of alimentary elements that are maintained in a sequence and can be modified by the addition of entities and removal of entities from the sequence via an interactive interface with a user. In non-limiting illustrative examples, the queue may have an "active end" and a "reserve end," wherein the active end is the 'most appropriate alimentary element' to be displayed such as by location, or some other discriminating criteria that has been determined by computing device 104 in a nearby originator; additionally, there may be related alimentary elements that are in the queue "behind" the first active end alimentary element and alternatives nearer the reserve end. In further non-limiting illustrative examples, a user may indicate via the graphical user interface that they do not want an alimentary element, whereby computing device 104 may remove it from the active end and push up by one place the next alimentary elements in the queue. In such an example, computing device 104 may add a newly generated alimentary element to the reserve end to maintain a list that a user may view, scroll through, or the like. Computing device 104 may locate an originator for each alimentary element in the queue; alternatively or additionally, computing device 104 may restrict searches to the most 'active end' entity in the queue or to an alimentary element that a user as selected.

Continuing in reference to FIG. 1, generating the queue of alimentary elements may include selecting the alimentary element originator and retrieving a plurality of alimentary elements from at least a located alimentary element originator. Locating the originator may include selection based on location, such as proximity to a first position. Locating the originator may include identifying compatible alimentary elements in the originators inventory, menu, item lists, etc., and selecting the originator as a function of retrieving a particular number of compatible options. Computing device 104 may iteratively locate and retrieve alimentary elements from originators using a variety of criteria, as described above, wherein retrieval includes locating particular data (alimentary element identity, prices, ingredients list, nutrition facts, Cuisine-type, online reviews, etc.) wherein the data is stored in non-transitory memory on the computing device 104 that may be selected to be displayed and arranged on the extensible alimentary element display 120. In non-limiting illustrative examples, computing device 104 may retrieve alimentary elements using a word, or term-based query, wherein the user has selected an alimentary element such as "salad", and computing device 104 locates originators based on a combination of user location and items listed as "salad". In such an example, all alimentary elements with "salad" in the name may be retrieved, along with accompanying data; alternatively or additionally, alimentary elements with "salad" may be further filtered or sorted prior to being retrieved, for instance based on nutrition content.

Continuing in reference to FIG. 1, generating the queue of alimentary elements may include calculating, using a machine-learning process 124, a plurality of nutrition metrics for the plurality of alimentary elements as a function of the nutrition content. A "nutrition metric," as used in this disclosure, is any qualitative and/or quantitative metric that describes nutritional value of an alimentary element for an individual. Nutrition metric 128 may include a qualitative metric, or signifier, such as "healthy", "not healthy," "choose", "avoid", and the like. Nutrition metric 128 may include a quantitative metric, such as a numerical value that signals the caloric content, macronutrient content such as effect on increasing blood sugar level, micronutrient effect on disease content such as iron content for addressing anemia, among other categories. Nutrition metric 128 may include data relating to the nutrition content as calculated from the 'nutrition facts label' of an alimentary element and a nutritional standard such as the 'recommended daily allowance based on 2,000 calories. Nutrition metric 128 may include a percentile that ranks alimentary elements relative to other available options, for instance without limitation, where a 'chimichanga' may be a 60$^{th}$ percentile option for healthy Mexican cuisine but 'tampiqueño' is 85$^{th}$ percentile. As used in this disclosure, "nutrition content," is any qualitative and/or quantitative value or descriptor that relates to the nutrition content of an alimentary element. Nutrition content may include qualitative descriptors such as "no appreciable amount." Nutrition content may include numerical values such the mass in grams of macronutrients/micronutrients per serving size, percent of a recommended daily allowance, etc.

Continuing in reference to FIG. 1, machine-learning process 124 may include any machine-learning process, model, and/or algorithm performed by a machine-learning module, as described in further detail below. A "machine learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language. Training data for a machine-learning process 124 may be used for generating a machine-learning model using the training data. Training data may include recommended daily allowances of macronutrients (carbohydrates, fats, and protein), micronutrients (water-soluble vitamins, fat-soluble vitamins, trace metals, co-factors, etc.), and the like, that is recommended of a particular user, such as based on a standard 2,000 calorie diet, ketogenic diet, vegan diet, Atkins diet, etc. Training data may include data retrieved from originators, including nutrition facts, where an entire menu of alimentary elements and the recommended daily allowance may be used to generate nutrition metrics 128 that would place each alimentary element on a numerical value scale, such as a standard percentile (0-100) scale for direct comparison between alimentary elements.

Continuing in reference to FIG. 1, a machine-learning process 124 may generate a plurality of nutrition metrics 128 by using training data to generate a machine-learning model, wherein the machine-learning model contains correlations, heuristics, and/or any mathematical relationships that may be determined from the training data. Machine-learning algorithm may include a supervised machine-learning algorithms, such as linear regression, k-nearest neighbors, naïve Bayes, neural networks, among other suitable supervised learning algorithms. Machine-learning algorithm may include unsupervised machine-learning algorithms, such as dimensionality reduction, clustering algorithms, among other suitable unsupervised learning algorithms. Calculating nutrition metric 128 using a machine-learning algorithm may include generating a graphical analysis describing, for instance and without limitation, the average caloric content per menu item, average micronutrient deficiency per cuisine type, among other relationships. In such an example, alimentary elements may be clustered into distinct queues based on these trends (for instance, diabetes-compatible cuisine types, anemia-addressing cuisine types, high-protein cuisine types) for displaying to the users. Alimentary elements may be placed into a queue as a function of a nutrition metric 128, such as an "edible score," which reflects the nutritional impact of an alimentary element and potential effect on a user's health, such as is determined and described in U.S. Nonprovisional application Ser. No. 16/983,034 filed on Aug. 3, 2020, and entitled "METHODS AND SYSTEMS FOR CALCULATING AN EDIBLE SCORE IN A DISPLAY INTERFACE," the entirety of which is incorporated herein by reference. An edible score may be a numerical value that described the nutrition content of an alimentary element and may be used for ranking, weighting, or otherwise filtering alimentary elements, for instance according to a threshold value, for building a queue. Such a queue may direct the extensible alimentary element display 120 as to which alimentary elements to display to second user and in what order.

Continuing in reference to FIG. 1, the plurality of alimentary elements may be sorted according to nutrition content. Alimentary elements may be displayed to the second user as a function of nutrition content, wherein alimentary elements may be sorted, ranked, and/or weighted based on nutrition metric 128. Alimentary elements may be sorted using a ranking function. Ranking function may include using computing device 104 to arrange alimentary elements in a particular ordering, or rank, based on the nutrition metrics 128, for instance from greatest numerical value to least. A ranking function may include machine-learning algorithms, processes, and/or models where alimentary elements with corresponding nutrition metrics 128 are used as inputs and an output of an ordered, or ranked, set of alimentary elements is generated based on relationships captured in a machine-learning model from training data. In such a case, training data may include a plurality of past selected alimentary elements by "guest users" (multiple users that are not the first user), wherein a plurality of alimentary elements that are commonly selected alongside compatible alimentary elements may receive a higher ranking (weighted) than nutrition metric 128 would imply. Ranking criterion used by machine-learning process may include additional data alongside nutrition content such as meal-type, Cuisine-type, price, or the like. A machine-learning process used for accepting inputs and generating a ranked output as a function of some criteria may include any algorithm described herein, as described in further detail below. Ranking alimentary elements may assist extensible alimentary element display 120 in 'knowing' which alimentary elements to place into a queue, in which order to place into the queue, and which to display to the first user and/or second user.

Continuing in reference to FIG. 1, generating the queue of alimentary elements may include filtering the plurality of alimentary elements as a function of the plurality of nutrition metrics 128 and a threshold value. A "threshold value," as used in this disclosure, is a qualitative and/or quantitative value, or criterion, used for determining which alimentary elements to place into a queue. In non-limiting illustrative examples, threshold value 132 may include a qualitative criterion such as "breakfast type elements," wherein only alimentary elements that are include identification data signifying "breakfast" are placed into the queue, whereas other alimentary elements that would otherwise be displayed are stored in a database 136. In such a case, alimentary elements (ranked or not) may be filtered for the extensible alimentary element display 120 using a defining term. In further non-limiting illustrative examples, threshold value 132 may include a quantitative value such as "only alimentary elements above a nutrition metric 128 of '70'," wherein only alimentary elements with nutrition metrics 128 above a certain numerical value are included into the queue. In such a case, alimentary elements (ranked or not) may be filtered for the extensible alimentary element display 120 using nutrition content as signified by a nutrition metric 128. Computing device 104 may set a threshold value 132, for instance and without limitation, as a function of user interaction with a user device and build an alimentary element queue 140 as a function of the threshold value 132.

Figure 2:
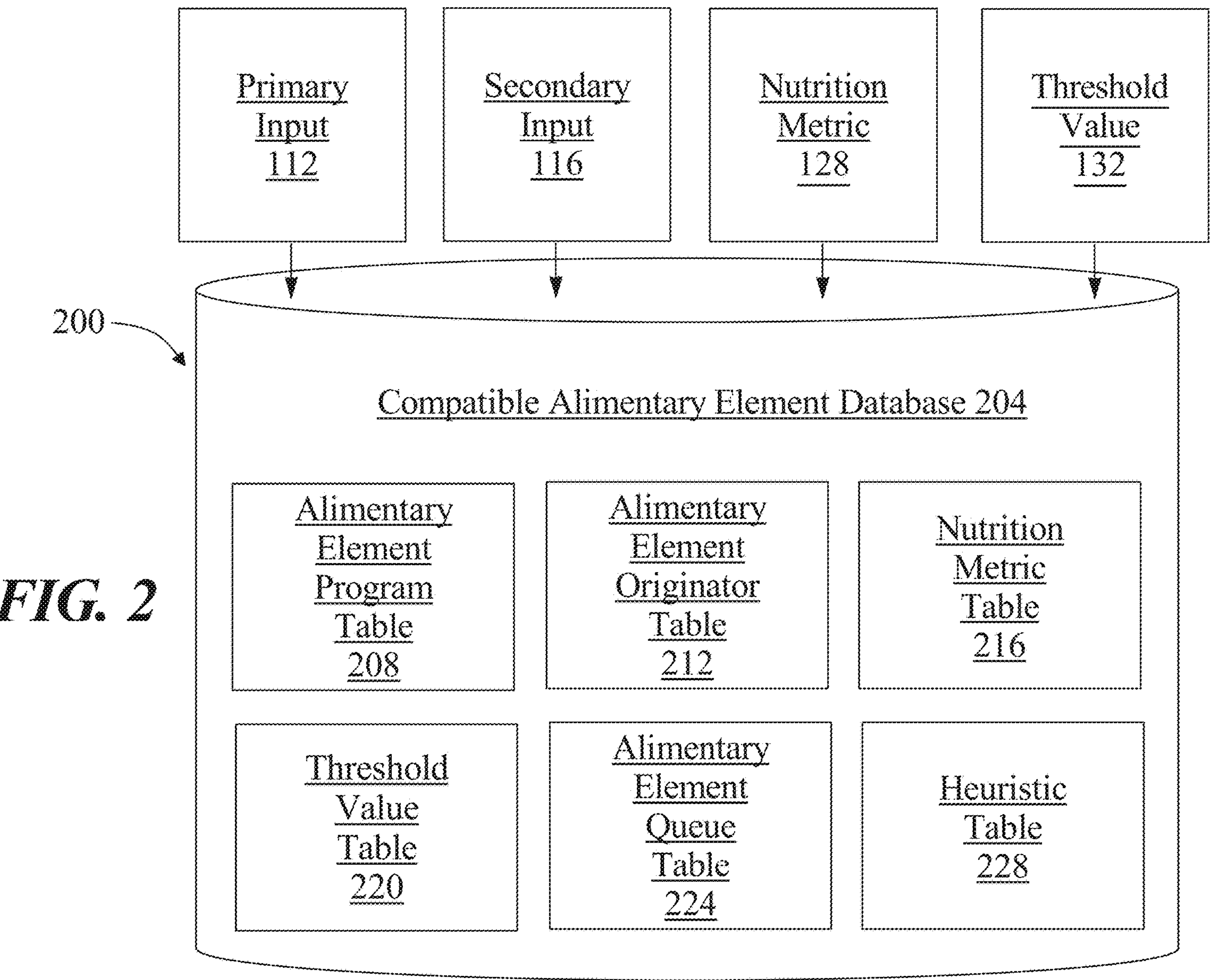
FIG. 2 is a block diagram illustrating an exemplary embodiment of an alimentary database.

Referring now to FIG. 2, an exemplary embodiment 200 of a compatible alimentary element database 204 is illustrated. Alimentary elements for the second user may include being stored in compatible alimentary element database 204. Compatible alimentary elements from an alimentary element program 108 for a first user may also be stored and/or retrieved from a compatible alimentary element database 204. Computing device 104 may store and/or retrieve primary input 112, secondary input 116, alimentary element data, first position data, compatible alimentary elements, nutrition metrics 128, among other determinations, I/O data, and the like, in a compatible alimentary element database 204. Compatible alimentary element database 204 may be implemented, without limitation, as a relational database, a key-value retrieval database such as a NOSQL database, or any other format or structure for use as a database that a person skilled in the art would recognize as suitable upon review of the entirety of this disclosure. Compatible alimentary element database 204 may alternatively or additionally be implemented using a distributed data storage protocol and/or data structure, such as a distributed hash table and the like. Compatible alimentary element database 204 may include a plurality of data entries and/or records, as described above. Data entries in a compatible alimentary element database 204 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure. Computing device 104 may retrieve any determinations, as described herein, from the compatible alimentary element database 204, such as ranked alimentary elements, threshold values 128, nutrition metrics 128, located originators, and the like.

Further referring to FIG. 2, compatible alimentary element database 204 may include, without limitation, alimentary element program table 208, alimentary element originator table 212, nutrition metric table 216, threshold value table 220, alimentary element queue table 224, and/or heuristic table 228. Determinations by a machine-learning process, machine-learning model, ranking function, and/or mapping application, may also be stored and/or retrieved from the compatible alimentary element database 204, for instance in non-limiting examples, alimentary element originators located as a function of a first position, the first position, and originators that a user preferably frequents. As a non-limiting example, compatible alimentary element database 204 may organize data according to one or more instruction tables. One or more compatible alimentary element database 204 tables may be linked to one another by, for instance in a non-limiting example, common column values. For instance, a common column between two tables of compatible alimentary element database 204 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 2, in a non-limiting embodiment, one or more tables of a compatible alimentary element database 204 may include, as a non-limiting example, an alimentary element program table 208, which may include categorized identifying data, as described above, including compatible alimentary element identities, nutrition content, originator identities, prices, Cuisine type, meal type, and the like. One or more tables may include alimentary element originator table 212, which may include data regarding originators used in the past, originators that offer compatible alimentary elements and those that do not, originators organized by Cuisine type, meal type, price, etc., that system 100 may use to retrieve and/or store alimentary element originator locations, menus, identities, and the like. One or more tables may include nutrition metric table 216, which may include nutrition metrics 128, nutrition content of alimentary elements, the identities of the alimentary elements, and the like, that system 100 may use for determining nutrition metrics 128. One or more tables may include threshold value table 220, which may include files of threshold values 128, past threshold values 128, and the like, as described above for instance and without limitation, that system 100 may use to retrieve, sort, and/or store, for filtering alimentary elements. One of more tables may include an alimentary element queue table 224, which may include instructions, numerical values, and/or outputs, determinations, variables, and the like, organized into subsets of data for generating instructions for how to build alimentary element queue 140 for extensible alimentary element display 120. One or more tables may include, without limitation, a heuristic table 228, which may organize rankings, scores, models, outcomes, functions, numerical values, arrays, matrices, and the like, that represent determinations, probabilities, metrics, parameters, and the like, include one or more inputs describing potential mathematical relationships, as described herein.

Figure 3:
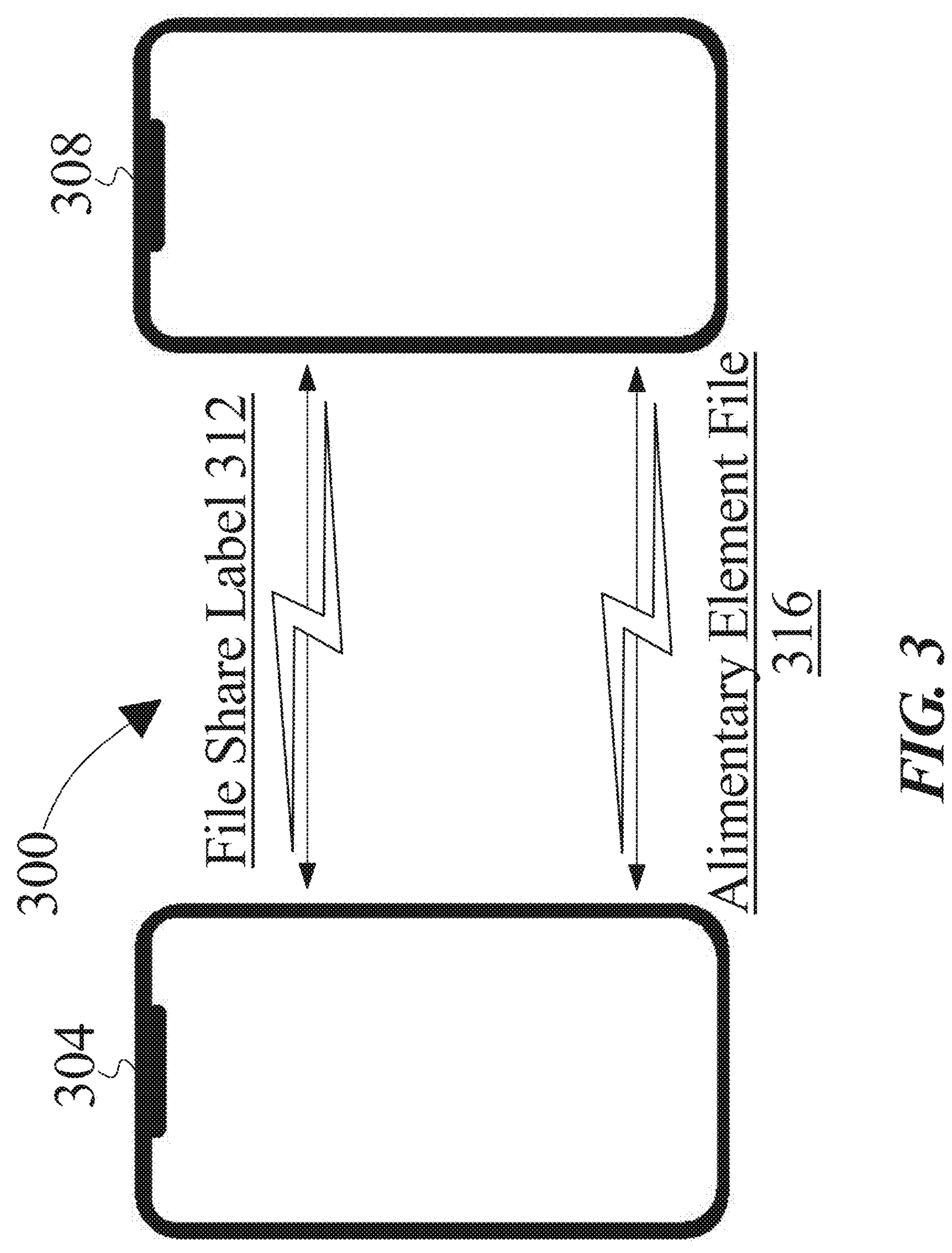
FIG. 3 is a diagrammatic representation of an exemplary embodiment of a file share label.

Referring now to FIG. 3, a non-limiting exemplary embodiment 300 of generating a file share label for transmitting an alimentary element file between devices is illustrated. Providing a representation of at least a compatible alimentary element for the first user and at least an alimentary element for the second user may include generating a file share label. A "file share label," as used in this disclosure, is an access token containing security credentials computing devices and/or user devices may use to identify one another and communicate. Computing device 104 may establish communication with at least a user device (such as a first device 304 and a second device 308) by generating a file share label 312. Computing device 104 may generate a unique file share label 312 for each device and/or may establish a file share label 312 for all user devices communicating with computing device 104. Computing device 104 may generate and transmit a file share label 312 to authenticate with a plurality of user devices and/or for the plurality of user devices to communicate with a compatible alimentary element database 204. File share label 312 may include an identifier associated with a logon session, wherein the identifier contains credentials to initiate communication between a first device 304 and a second device 308. Persons skilled in the art, upon reviewing the entirety of this disclosure, will be aware of various ways in access tokens may be generated and shared among devices.

Still referring to FIG. 3, a file share label 312 may include communication exchange such as a 'telecommunication handshake' that includes an automated process of communications between two or more devices, such as a first device 304 and a second device 308. A telecommunication handshake includes the exchange of information establishing protocols of communication at the start of communication before full communication commences. A telecommunication handshake may include exchanging signals to establish a communication link as well as to agree as to which protocols to implement. A telecommunication handshake may include negotiating parameters to be utilized between subject user device and computing device 104, including information transfer rate, coding alphabet, parity, interrupt procedure, and/or any other protocol or hardware features. A telecommunication handshake may include but is not limited to a transmission control protocol (TCP), simple mail transfer protocol (SMTP), transport layer security (TLS), Wi-Fi protected access (WPA), and the like.

Continuing in reference to FIG. 3, providing a representation of at least a compatible alimentary element for the first user and at least an alimentary element for the second user may include transmitting an alimentary element file from a first device 304 associated with the first user to a second device 308 associated with the second user, wherein the alimentary element file contains instructions for representing, via a graphical user interface, the alimentary element on the second device. An "alimentary element file," as used in this disclosure, is a data file containing instruction for representing alimentary elements on the second device 308 as a function of what is displayed on a first device 304. An alimentary element file 312 may include data for guiding what to display from a first user to a plurality of "guest" users. In this way, data describing what is displayed to a second user is sent to the second user device. An alimentary element file 312 may include originators displayed as a function of a first position associated with at least a first user, second user, and/or plurality of users, as described above. An aliment element file 312 may include nutrition metrics 128 associated with the displayed alimentary elements organized into a queue. An alimentary element file 312 may be transmitted using any radio frequencies and electromagnetic frequencies between approximately 20 kHz and approximately 300 GHz intended for communication between electronic devices, for instance as commonly used between network interfaces and local wireless communication. In exemplary embodiments, file share label 312 and/or alimentary element file 312 may include radio frequency (RF) transceiver components for accessing wireless voice and/or data networks (for instance, using cellular telephone technology, data network technology such as 3G, 4G/LTE, Wi-Fi (IEEE 802.11 family standards), or other mobile communication technologies, or any combination thereof), components for short-range wireless communication (for instance, using Airdrop, Bluetooth and/or Bluetooth LE standards, NFC, etc.), and/or other components. Network interface may provide wired network connectivity (such as Ethernet) in addition to and/or instead of a wireless interface. Network interface may be implemented using a combination of hardware (for instance, driver circuits, antennas, modulators/demodulators, encoders/decoders, and other analog and/or digital signal processing circuits) and software components. Network interface may support multiple communication channels concurrently, using the same transport or different transports, as necessary.

Continuing in reference to FIG. 3, computing device 104 is configured to provide a representation via the extensible alimentary element display 120 of at least a compatible alimentary element for the first user and at least an alimentary element for the second user as a function of the queue of alimentary elements. Alimentary element file 312 may include at least a compatible alimentary element, for instance as retrieved from an alimentary element program 108 intended for first user. Alimentary element file 312 may include at least an alimentary element for second user. Alimentary element file 312 may include an alimentary element queue 140 for directing extensible alimentary element display 120 to 'know' which alimentary elements to display, and in which order. Alimentary element file 312 may include data for the representation via the extensible alimentary element display 120, including order time, nutrition metric 128, nutrition facts, biological extraction (for a first user), and the like. A representation via the extensible alimentary element display 120 may be generated using any user interface and/or graphical user interface, as described above, including graphics, textual output, and the like.

Figure 4:
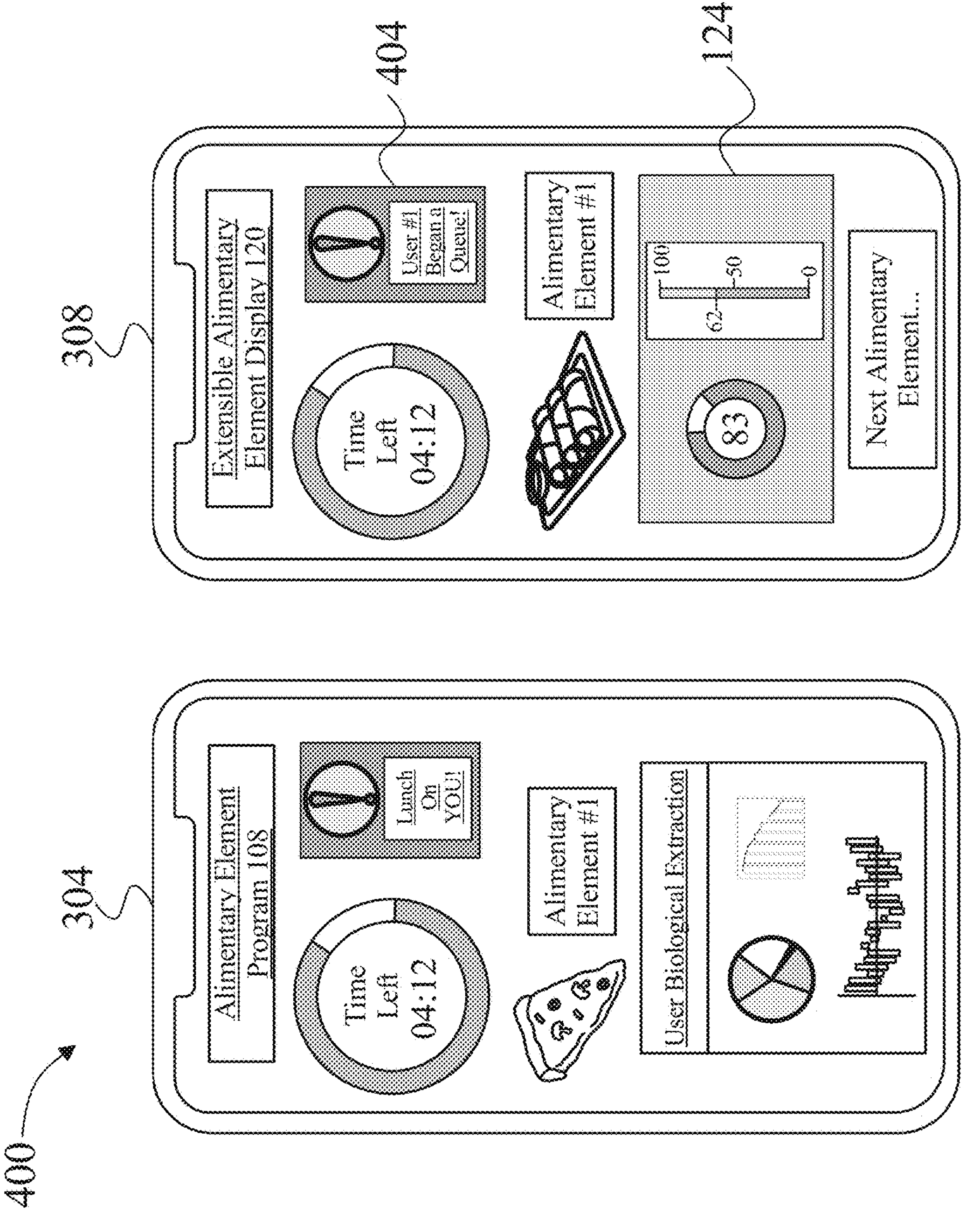
FIG. 4 is a diagrammatic representation of an exemplary embodiment of a first device signaling to a second device via an audiovisual notification.

Referring now to FIG. 4, a non-limiting exemplary embodiment 400 of an indication of the alimentary element by a respective interaction by the first user with the first device is signaled to the second device via an audiovisual notification is illustrated. In some embodiments, embodiment 400 may include a notification 404. A "notification," for the purposes of this disclosure is an alert that conveys information. An "audiovisual notification," as used in this disclosure, is a piece of information that alerts a user to an alimentary element. An audiovisual notification 404 may be a textual alert, a graphic, a vibration alert, a sound, or any other audiovisual notification, haptic feedback from a user device, or combination thereof, that computing device 104 may provide a user. Audiovisual notification 404 may include addressing the first user to select an alimentary element by a first device 304, for instance from the plurality of compatible alimentary elements from an alimentary element program 108. Audiovisual notification 404 may include addressing the second user to select an alimentary element by a second device 308, for instance from the plurality of alimentary elements in a queue in the extensible alimentary element display 120. Audiovisual notification 404 may include prompting the user to provide input, such as a cuisine type (Korean food), meal type (dinner), diet type (Paleo diet), price range (<$30 per entrée), and the like. Audiovisual notification 404 may include alerting a user to a potential allergen (shellfish, tree nuts, etc.), food intolerance (lactose, gluten, etc.), or other alimentary element consideration. Audiovisual notification 404 may include nutrition metric 128 information. Audiovisual notification 404 may include a time period for which a plurality of users may submit alimentary elements as "guests" to a first device 304 that initiated ordering.

With continued reference to FIG. 4, notification 404 may include a completion notification. A "completion notification," for the purposes of this disclosure, is a notification configured to alert a user that an alimentary element or plurality of alimentary elements are ready for consumption. For example, completion notification may be issued when one or more alimentary elements are delivered to a user. For example, completion notification may be issued when one or more alimentary elements are ready to be picked-up from an alimentary provider. Notification 404 may be displayed on first device 304 and/or second device 308.

With continued reference to FIG. 4, notification 404 may include a loop plating notification. "Loop plating notification," for the purposes of this disclosure, is a notification including information regarding a plate for an alimentary element. A "plate," for the purposes of this disclosure is an object that is used to serve or transport an alimentary element. Plate may include, as non-limiting examples, a dinner plate, a to-go box, a saucer, a platter, a lid for a platter, and the like. In some embodiments, plate may include a unique identifier. Unique identifier may include, as non-limiting examples, a bar code, a QR code, an RFID ID, an identification code, and the like. Unique identifier may be printed on a surface of plate. In some embodiments, unique identifier of plate may be scanned or otherwise processed by an alimentary provider. In some embodiments, this scanning/processing may be indicative of the plate being returned to the alimentary provider or service provider by a user. In some embodiments, loop plating notification may include a notification that a plate has been returned to an alimentary provider or service provider.

With continued reference to FIG. 4, in some embodiments, embodiment 400 may include a feedback field. A "feedback field," for the purposes of this disclosure, is a user interface element that is configured to collect feedback from a user. In some embodiments, feedback field may be configured to accept textual feedback. In some embodiments, feedback field may be configured to accept audio feedback; for example, user may be able to record their voice and submit a recording of their voice using feedback field. In some embodiments, feedback field may be configured to accept visual feedback; for example, a user may be able to upload an image using feedback field. In some embodiments feedback field may include a text box. In some embodiments, feedback field may be configured to receive a selection from a user. For example, this may include a selection of a rating out of 5, a selection indicating the user's mood or satisfaction, and the like. In some embodiments, feedback may include feedback regarding the quality of alimentary elements, the quality of service, whether the correct alimentary elements were delivered, and the like. Feedback field may be displayed on first device 304 and/or second device 308.

Referring now to FIG. 5, an exemplary embodiment 500 of locating alimentary element originators is illustrated. Radial search may be used for locating alimentary element originators as a function of the first position of a first user, second user, and/or plurality of users. Computing device 104 may use a radial search machine-learning process, as described herein, to locate alimentary element originators within a first radius. As depicted in FIG. 2A, radial search may select a first search radius to search based on a user first position (black-shaded circle), wherein a first circle (dashed line) of area about the user is searched for a suitable originator. In the event that a suitable originator is not located, the radius may widen to larger radii concentric rings (larger dashed-line rings). Alternatively or additionally, as depicted in FIG. 2B, a first radius may be searched about a first local solution that is a first alimentary element originator (black-shaded circle) until a better solution is located (grey-shaded circle), and in the even the alimentary originator is not suitable, or the user indicates a different alimentary element, or the solution is otherwise not optimal, a second radius may be searched, which may locate additional originators (white circle). Each additional search radii may be larger or smaller than a previous search radius but may include a different search center. Originator locations may be filtered as a function of both compatible alimentary elements and at least a second alimentary element suitable for a second user.

Figure 6:
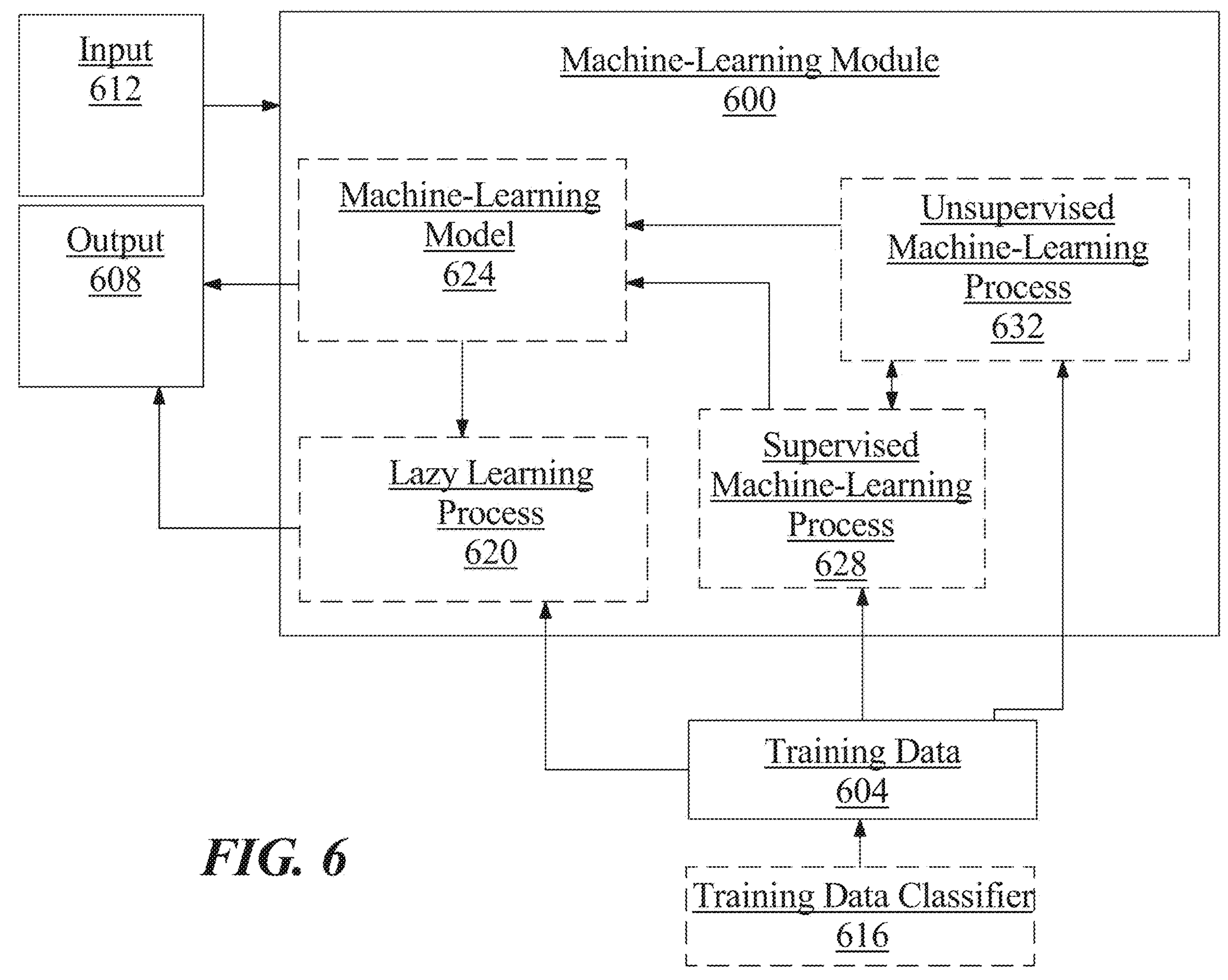
FIG. 6 is a block diagram illustrating an exemplary embodiment of a machine-learning module.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail herein. Training data 604 used by machine-learning module 600 may correlate any input data as described in this disclosure to any output data as described in this disclosure.

Further referring to FIG. 6, training data may be filtered, sorted, and/or selected using one or more supervised and/or unsupervised machine-learning processes and/or models as described in further detail herein; such models may include without limitation a training data classifier 616. Training data classifier 616 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 600 may generate a classifier using a classification algorithm, defined as a process whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to elements that characterizes a sub-population, such as a subset of alimentary elements as a function of nutrition metrics 128 or a subset of preferable originator locations and/or other analyzed items and/or phenomena for which a subset of training data may be selected.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements, such as ranking alimentary elements and building a queue as a function of some ranking association between elements (nutrition metric 128). Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 6, machine-learning processes as described in this disclosure may be used to generate machine-learning models 624. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used as a ranking function, as described above, to improve building an alimentary element queue 140 by "learning" which alimentary elements should be ranked above others based on, for instance, nutrition content, user preferences, locations, and the like.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a plurality of alimentary elements and nutrition metrics 128 as described above as inputs, a queue of alimentary elements as outputs, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 6, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 604.

Figure 7:
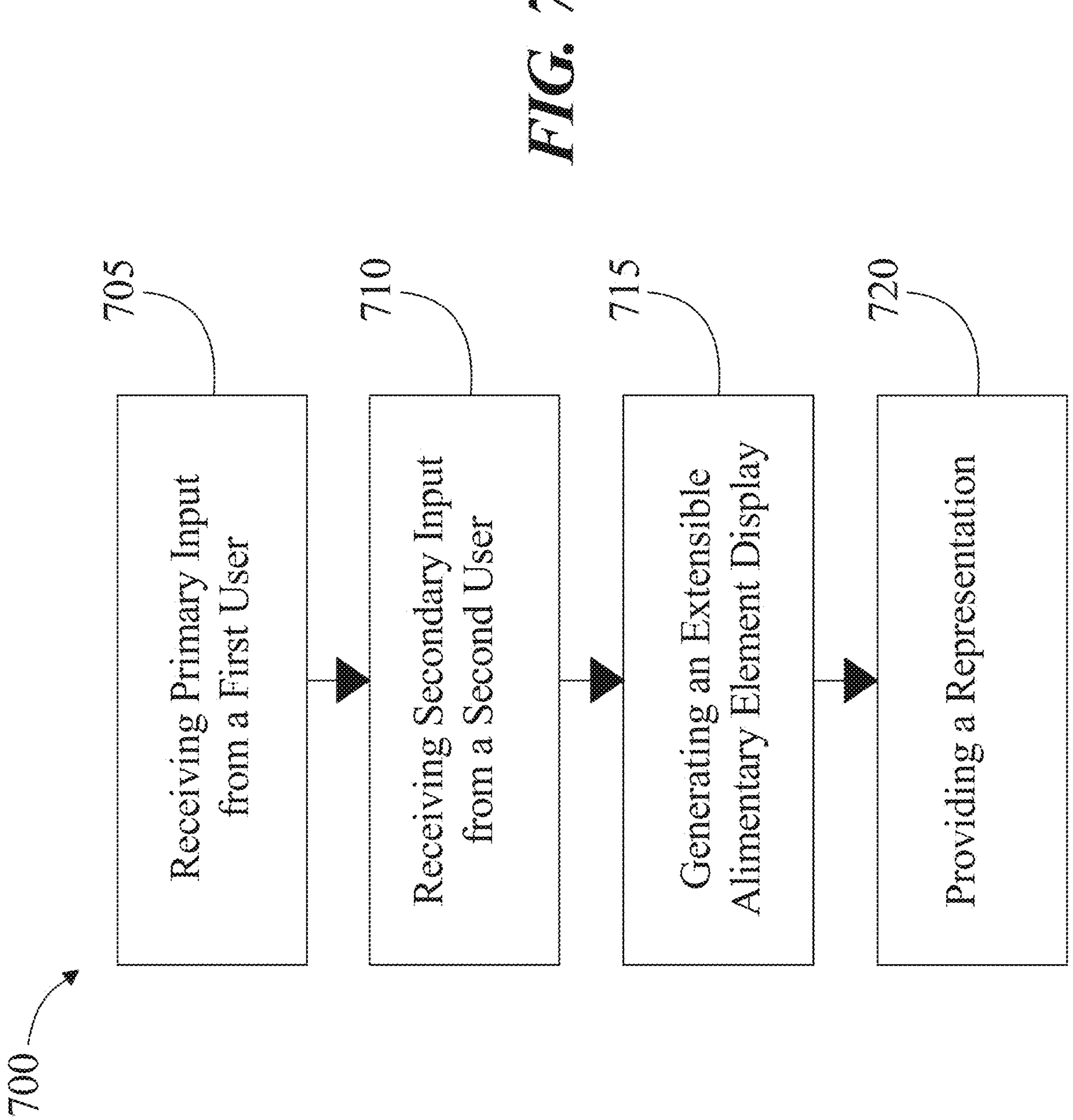
FIG. 7 is a flow diagram illustrating an exemplary method for providing alimentary elements.

Referring now to FIG. 7, an exemplary embodiment of a method 700 for providing alimentary elements is illustrated. At step 705, computing device 104 is configured for receiving primary input 112 relating to a first user for a compatible alimentary element, wherein compatible alimentary elements are based on biological extraction received from the first user; this may be implemented, without limitation, as described above in reference to FIGS. 1-6.

Continuing in reference to FIG. 7, at step 710, computing device 104 is configured for receiving secondary input 116 relating to a second user for an alimentary element, wherein the second user is not associated with an alimentary element program 108; this may be implemented, without limitation, as described above in reference to FIGS. 1-6.

Still referring to FIG. 7, at step 715, computing device 104 is configured for generating an extensible alimentary element display 120 for a second user, wherein generating the extensible alimentary element display 120 includes locating alimentary element originators as a function of a secondary input and the compatible alimentary elements for the first user as a function of a first position associated with the first user, and generating a queue of alimentary elements retrieved from the located alimentary element originators, wherein the queue includes alimentary elements for the second user as a function of the secondary input and the compatible alimentary elements provided to the first user. Locating alimentary element originators may include identifying the alimentary element originators as a function of proximity to the first position and sorting the alimentary element originators based on the ability to provide compatible alimentary elements. The extensible alimentary element display 120 for the second user may include an interactive graphical user interface that is configured to display alimentary elements on a second device associated with the second user as a function of what is displayed on a first device associated with the first user. Generating the queue of alimentary elements may include selecting the alimentary element originator and retrieving a plurality of alimentary elements from at least a located alimentary element originator. Generating the queue of alimentary elements may include calculating, using a machine-learning process, a plurality of nutrition metrics 128 for the plurality of alimentary elements as a function of the nutrition content. The plurality of alimentary elements may be sorted according to nutrition content. Generating the queue of alimentary elements may include filtering the plurality of alimentary elements as a function of the plurality of nutrition metrics 128 and a threshold value 132. The alimentary elements for the second user may be stored in compatible alimentary element database 204; this may be implemented, without limitation, as described above in reference to FIGS. 1-6.

Continuing in reference to FIG. 7, at step 720, computing device 104 is configured for providing a representation, via a graphical user interface, of at least a compatible alimentary element for the first user and at least an alimentary element for the second user. Providing a representation of at least a compatible alimentary element for the first user and at least an alimentary element for the second user may include generating a file share label 312 and transmitting an alimentary element file 316 from a first device 304 associated with the first user to a second device 308 associated with the second user, wherein the alimentary element file 316 contains instructions for representing, via a graphical user interface, the alimentary element on the second device 308. An indication of the alimentary element by a respective interaction by the first user with the first device 304 may be signaled to the second device 308 via an audiovisual notification 404; this may be implemented, without limitation, as described above in reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
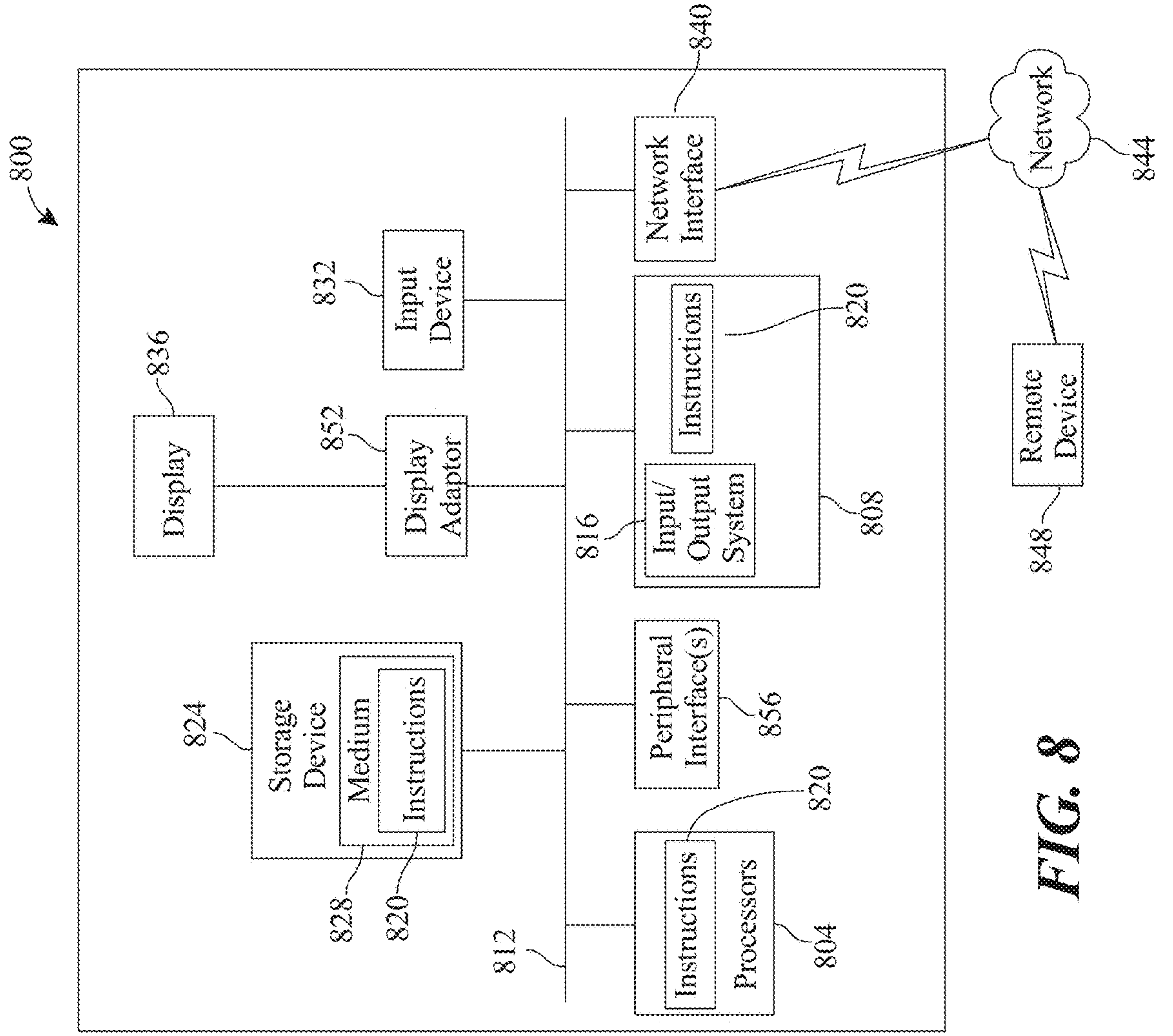
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for providing alimentary elements, the system comprising:

a computing device, wherein the computing device is configured to:

receive a primary input from a first user, wherein the primary input comprises a user input relating to the first user for a compatible alimentary element;

receive a secondary input from a second user, wherein the secondary input includes at least a request for the compatible alimentary element of the first user, wherein the secondary input comprises payment data;

generate an alimentary element program as a function of the compatible alimentary element and a biological extraction associated with the first user, and wherein the second user is not associated with the alimentary element program;

locate an alimentary element originator as a function of a first position associated with the first user and the compatible alimentary element;

generate a queue of a plurality of alimentary elements from the at least an alimentary element originator; and display the queue of the plurality of alimentary elements using a graphical user interface.

2. The system of claim 1, wherein the computing device is additionally configured to generate a nutrition metric for each alimentary element of the plurality of alimentary elements.

3. The system of claim 1, wherein generating the queue of the plurality of alimentary elements comprises filtering the plurality of alimentary elements as a function of a threshold value.

4. The system of claim 1, wherein locating the at least an alimentary element originator comprises:

selecting a first search radius as a function of a first position of the first user; and performing a radial search as a function of the first search radius.

5. The system of claim 4, wherein the queue of the plurality of alimentary elements comprises the plurality of alimentary elements sorted as function of proximity to the first position of the at least an alimentary element originator.

6. The system of claim 1, wherein locating the at least an alimentary element originator comprises:

training a radial machine learning model using training data, wherein the training data comprises the first position and the compatible alimentary element as inputs correlated to the alimentary element originator as an output; and locating the at least an alimentary element originator using the trained radial machine learning model.

7. The system of claim 1, wherein the computing device is additionally configured to provide a completion notification to the second user, wherein the completion notification is configured to notify the second user that at least an alimentary element of the plurality of alimentary elements is ready for consumption.

8. The system of claim 1, wherein the computing device is additionally configured to modify the alimentary element program as a function of a user preference.

9. The system of claim 1, wherein the computing device is additionally configured to generate an extensible alimentary element display for the second user.

10. The system of claim 9, wherein the extensible alimentary element display further comprises an interactive graphical user interface that is configured to display alimentary elements on a second device associated with the second user.

11. A method for providing alimentary elements, the method comprising:

receiving, using a computing device, a primary input from a first user, wherein the primary input comprises a user input relating to the first user for a compatible alimentary element;

receiving, using the computing device, a secondary input from a second user, wherein the secondary input includes at least a request for a compatible alimentary element of the first user, wherein the secondary input comprises payment data;

generating, using the computing device, an alimentary element program as a function of the compatible alimentary element and a biological extraction associated with the first user, and wherein the second user is not associated with the alimentary element program;

locating, using the computing device, at least an alimentary element originator as a function of a first position associated with the first user and the compatible alimentary element;

generating, using the computing device, a queue of a plurality of alimentary elements from the at least an alimentary element originator, wherein the queue of alimentary elements comprises a plurality of alimentary element; and displaying the queue of a plurality of alimentary elements using a graphical user interface.

12. The method of claim 11, wherein the method further comprises generating, using the computing device, a nutrition metric for each alimentary element of the plurality of alimentary elements.

13. The method of claim 11, wherein generating the queue of the plurality of alimentary elements comprises filtering the plurality of alimentary elements as a function of a threshold value.

14. The method of claim 11, wherein locating the at least an alimentary element originator comprises:

selecting a first search radius as a function of a first position of the first user; and performing a radial search as a function of the first search radius.

15. The method of claim 14, wherein the queue of the plurality of alimentary elements comprises the plurality of alimentary elements sorted as function of proximity to the first position of the at least an alimentary element originator.

16. The method of claim 11, wherein locating the at least an alimentary element originator comprises:

training a radial machine learning model using training data, wherein the training data comprises the first position and the compatible alimentary element as inputs correlated to the alimentary element originator as an output; and locating the at least an alimentary element originator using the trained radial machine learning model.

17. The method of claim 11, wherein the method further comprises notifying, using the computing device, the second user that at least an alimentary element of the plurality of alimentary elements is ready for consumption using a completion notification.

18. The method of claim 11, wherein the method further comprises modifying, using the computing device, the alimentary element program as a function of a user preference.

19. The method of claim 11, wherein the method further comprises generating, using the computing device, an extensible alimentary element display for the second user.

20. The method of claim 19, wherein the extensible alimentary element display further comprises an interactive graphical user interface that is configured to display alimentary elements on a second device associated with the second user.

* * * * *